Oct. 10, 1939. S. JOHNSON Plant Pat. 342
LEMON TREE
Filed Dec. 13, 1938
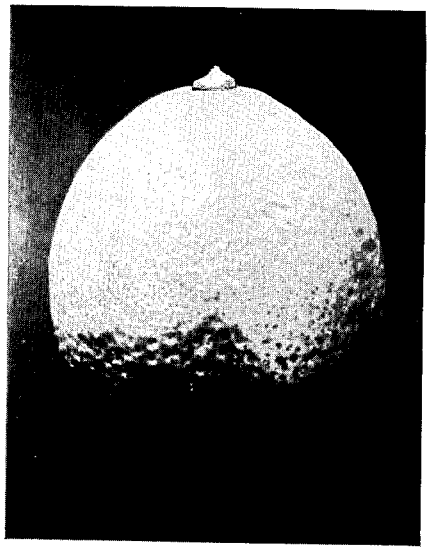
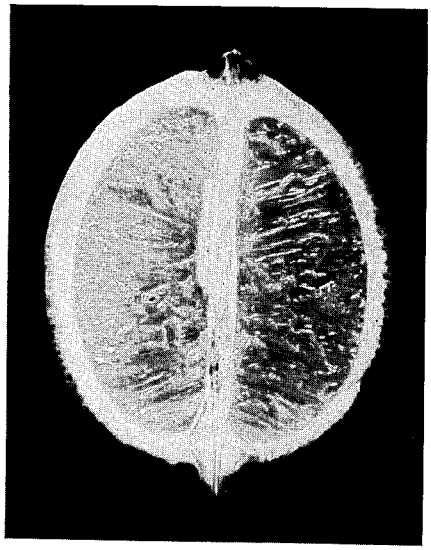
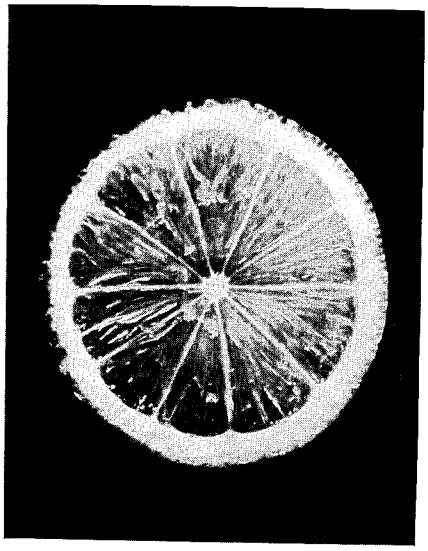
INVENTOR
Sanford Johnson
By Orville M Kile
Plant Patent Agent Patented Oct. 10, 1939

Plant Pat. 342

UNITED STATES PATENT OFFICE

342

LEMON TREE

Sanford Johnson, Riverside, Calif.

Application December 13, 1938, Serial No. 245,493

1 Claim. (Cl. 47—62)

My discovery relates to lemon trees and particularly to a new and distinct variety of lemon tree which is probably a sport of the variety Eureka. This new variety was first discovered by me many years ago on my property in Riverside, which I had purchased a number of years after the planting of the orchard of which this tree was a part. Inasmuch as it is not the custom to plant lemon seedlings in orchard form in California, undoubtedly all of the trees in this orchard were budded trees. I feel certain, therefore, that the variety originated as a whole-tree bud sport, probably of the variety Eureka. During the past three years, buds from the original tree-sport have been used for asexual reproduction and the resulting trees show the same properties as the original tree-sport.

My new variety somewhat resembles the Eureka but differs from it in several important respects. The principal difference lies in the absolute absence of seeds in my new variety. Over a period of years no seed has ever been found in any fruit of my new variety, and prolonged observation indicates that this characteristic is permanent both in the original tree-sport and in the specimens which have been asexually reproduced from the original tree. The Eureka lemon usually contains two or three seeds and although it may occasionally produce a fruit which is seedless, other fruits on the same tree at some time during the year, will be found to have seeds.

Another notable difference between these two varieties is the complete absence of pollen from the flowers of my new variety, a characteristic which is not present in the variety Eureka.

Also notable is the great vigor of my new variety as compared with that of Eureka. In California Eureka trees are not vigorous as compared with most other lemon trees, but trees of my new variety show an unusually vigorous condition as compared with Eureka. Neither have my new trees ever shown any damage from frost, even though located in a position where Eureka trees show damage under normal conditions. Cold resistance has been observed in the original sport tree for many years and during the past three years in the trees asexually reproduced from this original sport. In the severe freeze experienced in 1937, both the original tree and the newer trees of this variety were damaged only in a very minor degree while Eureka trees within two or three blocks were severely damaged.

The accompanying illustration gives in black and white, a side view of one of the fruits of my variety, a longitudinal cross-section, and a transverse cross-section.

Following is a detailed description of this new variety of lemon tree. Where colors are mentioned, the ordinary dictionary term is intended.

*Tree and flowers*

*Growth.*—Vigorous; spreading; highly productive.

*Size.*—Medium.

*Fruiting season.*—Continuous bearer, ripening its fruit throughout the year.

*Cold resistance.*—Good compared to similar varieties.

*Trunk.*—Stocky; disease free.

*Branches.*—Strong; willowy, tending to droop with the weight of the fruit.

*Leaves.*—Size—three to five inches long on mature wood, seven to nine inches long on new wood. Shape—oblong-lanceolate; edge serrate. Color—dark green above, light green below. Petioles—lacking.

*Flowers.*—Borne throughout the year. Arrangement—borne in clusters. Color—white shading to pink. Pollen—entirely lacking.

*Fruit*

*Size.*—Uniform; 2¾ to 3¼ inches long, 2 to 2⅜ inches across.

*Shape.*—Elongated globe; base tapering; apex nippled.

*Rind.*—Smooth; glossy.

*Juice.*—Very abundant; rich; clear; highly acid.

*Flavor.*—Excellent.

*Seeds.*—Absolutely none.

*Segments.*—Ten.

*Core.*—Tightly closed.

*Keeping and shipping qualities.*—Excellent.

*Comparison*

The variety known to me which most resembles my new variety is the Eureka which is presumably its parent. My new variety differs from the Eureka in the following important respects:

1. My new variety is entirely seedless while Eureka usually has two or three seeds.
2. The flower of my new variety is entirely without pollen, a characteristic which is not true of Eureka.
3. My new variety is much more vigorous than Eureka.
4. My new variety is more resistant to cold than is Eureka.

Having thus disclosed my discovery, I claim:

A new and distinct variety of lemon tree as described, characterized particularly by its vigorous growth; its relative resistance to cold; and the complete absence of pollen from its flowers and seeds from its fruits.

SANFORD JOHNSON.